United States Patent
Valkoun et al.

(10) Patent No.: US 11,638,650 B2
(45) Date of Patent: May 2, 2023

(54) STANDALONE ANTERIOR CERVICAL INTERBODY SPACER

(71) Applicant: Astura Medical Inc., Carlsbad, CA (US)

(72) Inventors: Anthony Valkoun, Carlsbad, CA (US); Thomas Purcell, Carlsbad, CA (US)

(73) Assignee: ASTURA MEDICAL INC, Irving, TX (US)

( * ) Notice: Subject to any disclaimer, the term of this patent is extended or adjusted under 35 U.S.C. 154(b) by 160 days.

(21) Appl. No.: 17/031,867

(22) Filed: Sep. 24, 2020

(65) Prior Publication Data
US 2021/0085476 A1 Mar. 25, 2021

Related U.S. Application Data

(60) Provisional application No. 62/905,381, filed on Sep. 24, 2019.

(51) Int. Cl.
*A61F 2/44* (2006.01)
*A61F 2/30* (2006.01)

(52) U.S. Cl.
CPC ............ *A61F 2/442* (2013.01); *A61F 2/4455* (2013.01); *A61F 2002/30092* (2013.01); *A61F 2002/30131* (2013.01); *A61F 2002/30331* (2013.01); *A61F 2310/00023* (2013.01)

(58) Field of Classification Search
CPC .......... A61F 2/44; A61F 2/442; A61F 2/4455; A61F 2/446; A61F 2/4465; A61F 2/447; A61F 2002/30092; A61F 2002/30131; A61F 2002/30331; A61F 2002/30352; A61F 2002/30428; A61F 2002/30429; A61F 2002/30476
See application file for complete search history.

(56) References Cited

U.S. PATENT DOCUMENTS

| | | | | |
|---|---|---|---|---|
| 7,850,731 B2* | 12/2010 | Brittan | ................. | A61F 2/4611 623/17.11 |
| 8,491,658 B1* | 7/2013 | Etminan | ............... | A61F 2/4611 623/17.16 |
| 9,848,994 B2* | 12/2017 | Petersheim | ............. | A61F 2/447 |
| 9,968,461 B2* | 5/2018 | Zappacosta | ........... | A61F 2/4455 |
| 10,179,053 B2* | 1/2019 | Zappacosta | ............. | A61F 2/447 |
| 10,925,750 B2* | 2/2021 | Zappacosta | ............. | A61F 2/447 |
| 11,207,196 B2* | 12/2021 | Donahoe | ................ | A61B 17/86 |
| 2002/0107537 A1 | 8/2002 | Steinberg | | |
| 2004/0193269 A1* | 9/2004 | Fraser | ................ | A61B 17/7059 623/17.11 |
| 2008/0306596 A1* | 12/2008 | Jones | ................. | A61B 17/8042 623/17.16 |
| 2010/0057206 A1* | 3/2010 | Duffield | .................... | A61F 2/44 606/279 |
| 2010/0312345 A1* | 12/2010 | Duffield | ................ | A61F 2/4455 623/17.16 |
| 2011/0251689 A1* | 10/2011 | Seifert | .................. | A61F 2/4465 623/17.16 |

(Continued)

OTHER PUBLICATIONS

Iternational Search Report in PCT Application No. PCT/US2020/052939 dated Dec. 17, 2020.

*Primary Examiner* — Eric S Gibson
(74) *Attorney, Agent, or Firm* — Michael R. Shevlin

(57) ABSTRACT

A standalone anterior cervical interbody spacer (ACIF) that includes a spacer body and plate rigidly couple via flexible pins.

20 Claims, 9 Drawing Sheets

(56) References Cited

U.S. PATENT DOCUMENTS

| | | | |
|---|---|---|---|
| 2012/0078373 A1* | 3/2012 | Gamache | A61B 17/8052 |
| | | | 623/17.16 |
| 2013/0006357 A1 | 1/2013 | Krueger | |
| 2013/0041408 A1 | 2/2013 | Dinville et al. | |
| 2013/0282125 A1* | 10/2013 | Etminan | A61F 2/447 |
| | | | 623/17.16 |
| 2014/0012380 A1* | 1/2014 | Laurence | A61F 2/447 |
| | | | 623/17.16 |
| 2014/0039623 A1* | 2/2014 | Iott | A61F 2/30744 |
| | | | 623/17.16 |
| 2014/0180422 A1* | 6/2014 | Klimek | A61F 2/30744 |
| | | | 623/17.16 |
| 2014/0228957 A1* | 8/2014 | Niemiec | A61F 2/4455 |
| | | | 623/17.16 |
| 2014/0228958 A1* | 8/2014 | Niemiec | A61B 17/86 |
| | | | 623/17.16 |
| 2014/0228959 A1* | 8/2014 | Niemiec | A61F 2/447 |
| | | | 623/17.16 |
| 2014/0257487 A1* | 9/2014 | Lawson | A61B 17/8042 |
| | | | 623/17.16 |
| 2014/0277497 A1* | 9/2014 | Bennett | A61F 2/4455 |
| | | | 623/17.16 |
| 2015/0328009 A1* | 11/2015 | Zappacosta | A61F 2/442 |
| | | | 623/17.16 |
| 2015/0328010 A1* | 11/2015 | Martynova | A61F 2/447 |
| | | | 623/17.16 |
| 2016/0095714 A1* | 4/2016 | Spangler | A61L 31/06 |
| | | | 623/17.16 |
| 2021/0085476 A1* | 3/2021 | Valkoun | A61F 2/442 |

\* cited by examiner

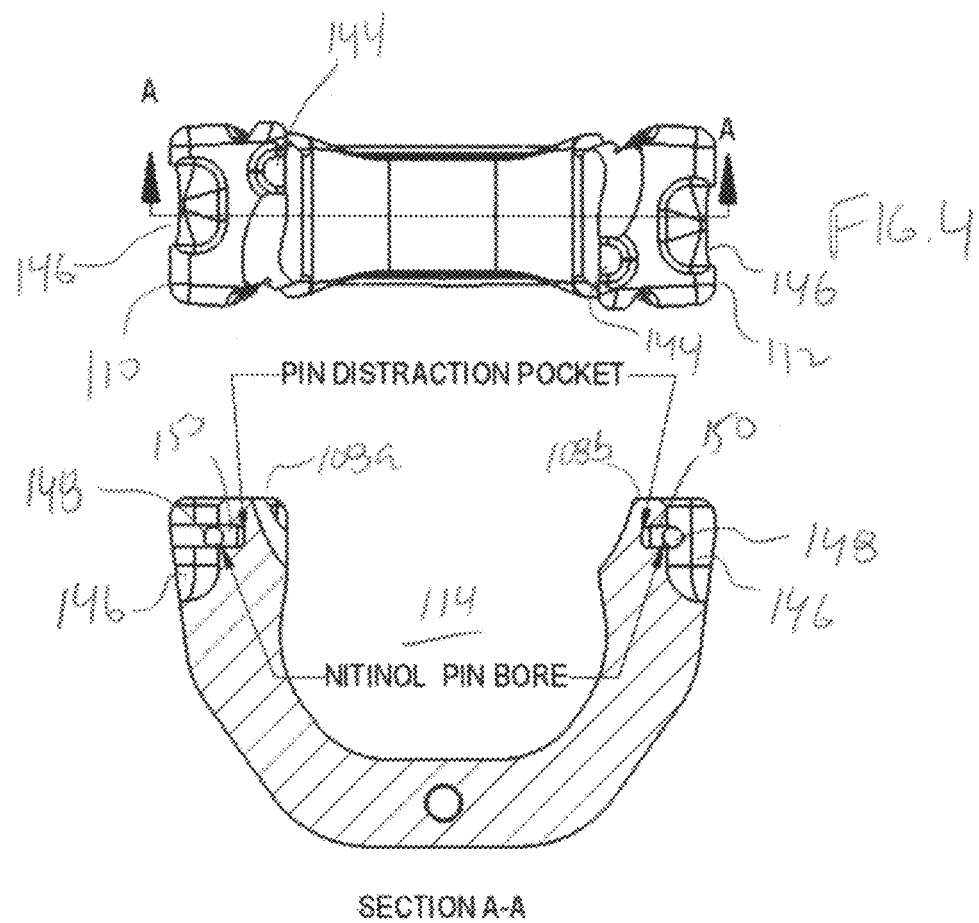
FIG. 4
FIG. 5
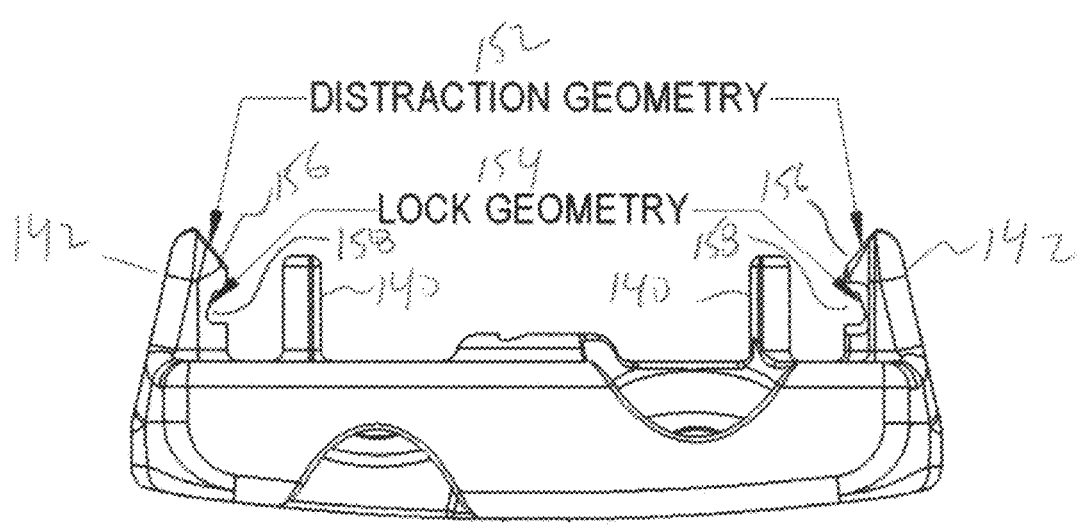
FIG. 6

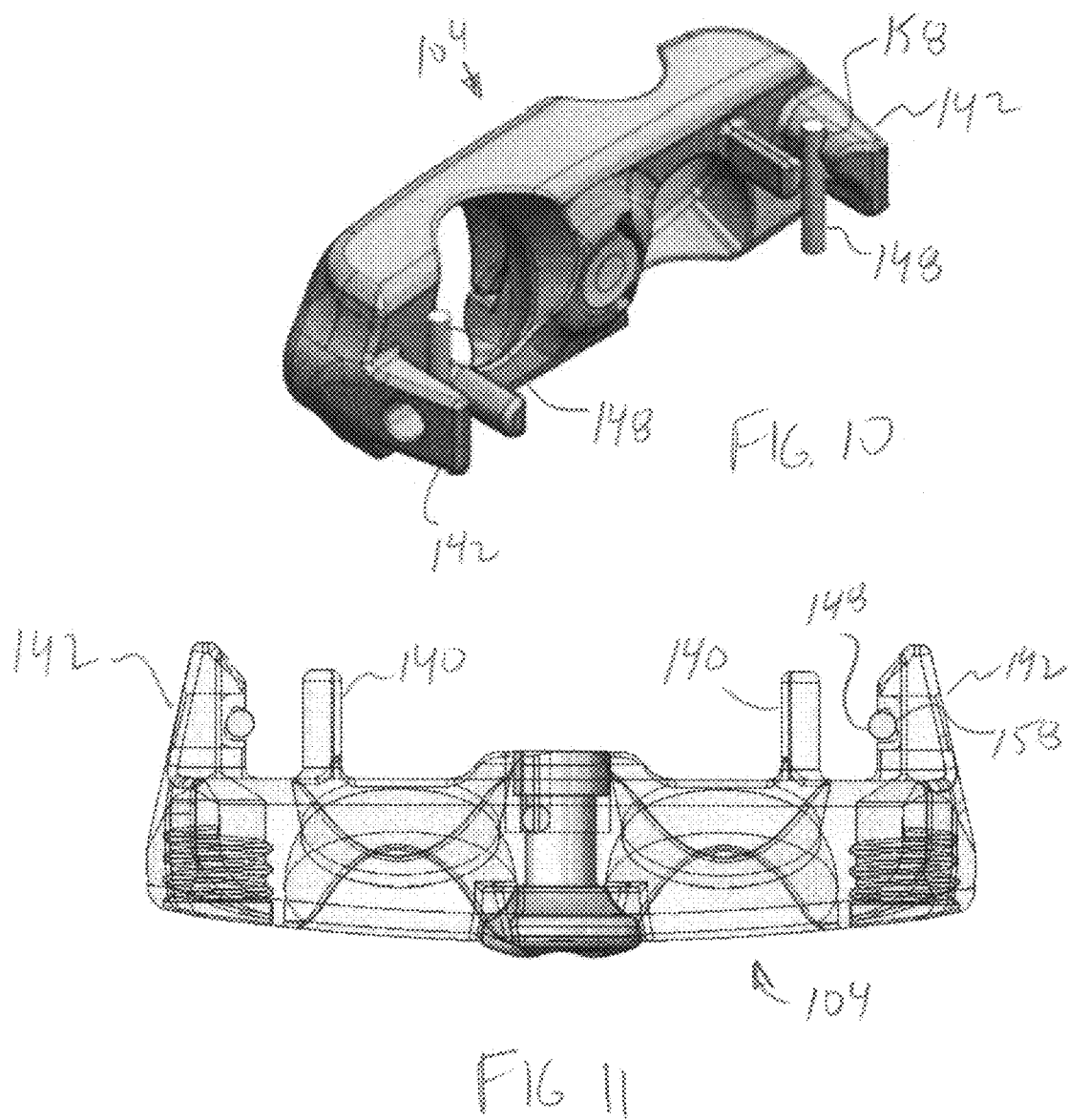

STANDALONE ANTERIOR CERVICAL INTERBODY SPACER

CROSS-REFERENCE TO RELATED APPLICATIONS

This application claims the benefit of U.S. Provisional Application No. 62/905,381 filed Sep. 24, 2019, which is incorporated herein by reference.

FIELD

The present invention relates generally to the field of surgery, and more specifically, to an anterior cervical interbody spacer for placement in intervertebral space between adjacent vertebrae during anterior cervical spinal fixation.

BACKGROUND

A spinal disc can become damaged as a result of degeneration, dysfunction, disease and/or trauma. Conservative treatment can include non-operative treatment through exercise and/or pain relievers to deal with the pain. Operative treatment options include disc removal and replacement using an interbody spacers such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The spacers are placed in the interdiscal space between adjacent vertebrae of the spine, resulting in spinal fusion of the adjacent vertebra wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is inserted in the space between the adjacent vertebrae.

Ideally, the interbody spacer should stabilize the intervertebral space and allow fusion of the adjacent vertebrae. Moreover, during the time it takes for fusion to occur, the interbody spacer body should have sufficient structural integrity to withstand the stress of maintaining the space without substantially degrading or deforming and have sufficient stability to remain securely in place prior to actual bone ingrowth fusion.

The interbody spacers are typically one piece that are assembled at the manufacturing stage. Many different sizes are made, which results in a large inventory of plate/spacer body combinations, as well as large sterilization/shipping caddies to facilitate transfer of spacers large interbody spacers. In addition, typical interbody spacers require a secondary element to install the plate in-situ to inhibit fixation screw migration. This secondary action is time consuming and cumbersome when the surgical procedure is time sensitive.

Some prior art designs utilized titanium arms for distraction, this places a large amount of force on the PEEK spacer body, potentially damaging the spacer during assembly. This increased distraction force requires a large assembly tool to overcome the titanium arms and makes disassembly difficult.

It would be desirable to provide an interbody spacer with modularity and functionality to decreased inventory size.

SUMMARY

Disclosed is a standalone anterior cervical interbody spacer that includes a spacer body and cervical plate with a unique locking system rigidly couple the spacer body and cervical plate via two flexible locking pins.

The locking system include locking features designed to engage with one or more flexible locking pins to lock the spacer body and cervical plate together. The locking features are part of the engagement arm or engagement protrusion with a locking pin engagement surface having distraction geometry and lock geometry. The distraction geometry includes an inclined or ramped portion and the lock geometry includes a pin engagement recess or pocket. The distraction geometry is such that as the spacer body and cervical plate are coupled, the inclined or ramped portion will engage and force the flexible pin to deform and slide on the surface. Once the cervical plate and spacer body are completely joined, the flexible pin reaches the lock geometry recess or pocket, allowing the flexible pin to return to its original form in the recess or pocket, thereby locking the spacer body and cervical plate. The pin engaging the recess may provide an audible click sound the let the user know that the parts are joined and locked together.

In some embodiments the flexible locking pins are positioned within the spacer body.

In some embodiments the flexible locking pins are positioned within the cervical plate.

BRIEF DESCRIPTION OF THE DRAWINGS

FIG. 4 shows a proximal view of the spacer body showing locking geometry FIG. 5 shows a sectional view at A-A of the spacer body shown in FIG. 4.

FIG. 6 shows a top view of the cervical plate.

FIG. 10 shows a perspective view of the cervical plate.

FIG. 11 shows a top view of the cervical plate.

DETAILED DESCRIPTION

The invention is direct to an anterior cervical interbody spacer that is a modular two piece design comprising a cervical spacer body and cervical plate that are designed to lock together via two flexible locking pins. With this design, each of the components are provided in various sizes and configurations so that the surgeon can pick or choose the desired spacer body configuration and size. The surgeon can then select the desired cervical plate configuration and join the two together. The spacer body and cervical plate have engagement features that are configured to rigidly couple them together via the flexible locking pins to form the cervical interbody spacer.

Figure 1:
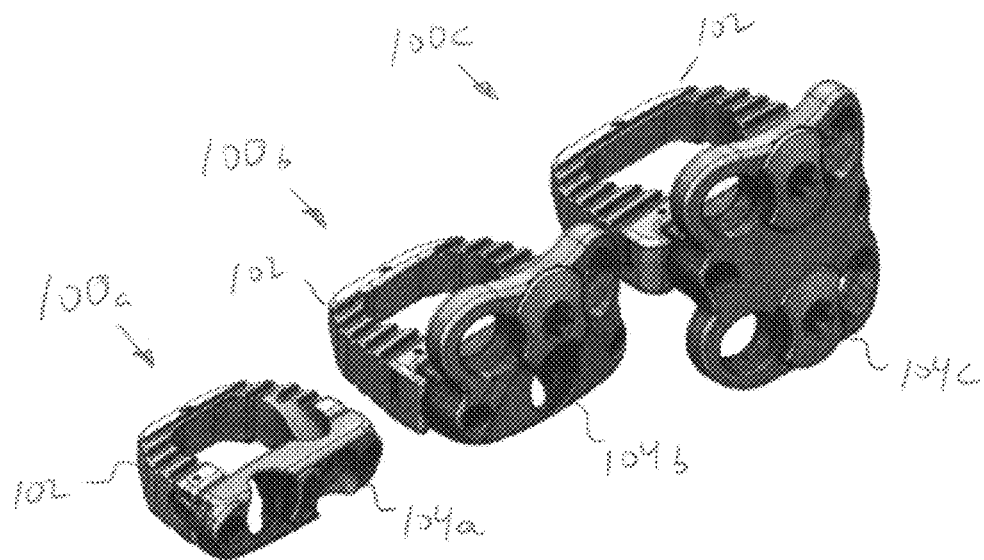
FIG. 1 shows various configurations or variations of a modular cervical interbody spacer having a cervical spacer body coupled with different cervical plates.

FIG. 1 shows three configurations or variations of a modular cervical interbody spacer 100 comprising a cervical spacer body 102 coupled with three different cervical plate configurations or profile options: Zero 104a, Half 104b, Full 104c.

Figure 2:
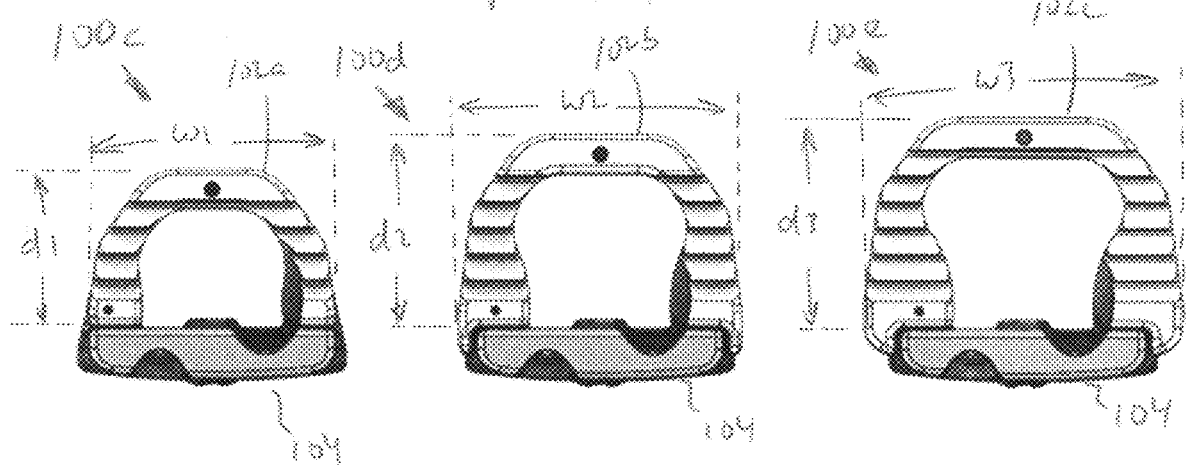
FIG. 2 shows various configurations or variations of a cervical interbody spacer with different cervical spacer body footprints or configurations coupled with a cervical plate.

FIG. 2 shows three configurations or variations of a cervical interbody spacer comprising a three different cervical spacer body footprints or configurations coupled with a cervical plate. The spacer body configurations may include various footprints having different widths W, depths D, heights and sagittal profiles. For example, spacer body 102a may be 14×12 mm, 102b may be 16×14 mm, and 102c may be 18×15 mm, the heights of the spacer body may include seven heights from 5 mm-12 mm @1 mm increments, and two sagittal profiles, 7°, 10°.

1$^{st}$ Embodiment—Flexible Locking Pins Positioned in the Spacer Body

Figure 3:
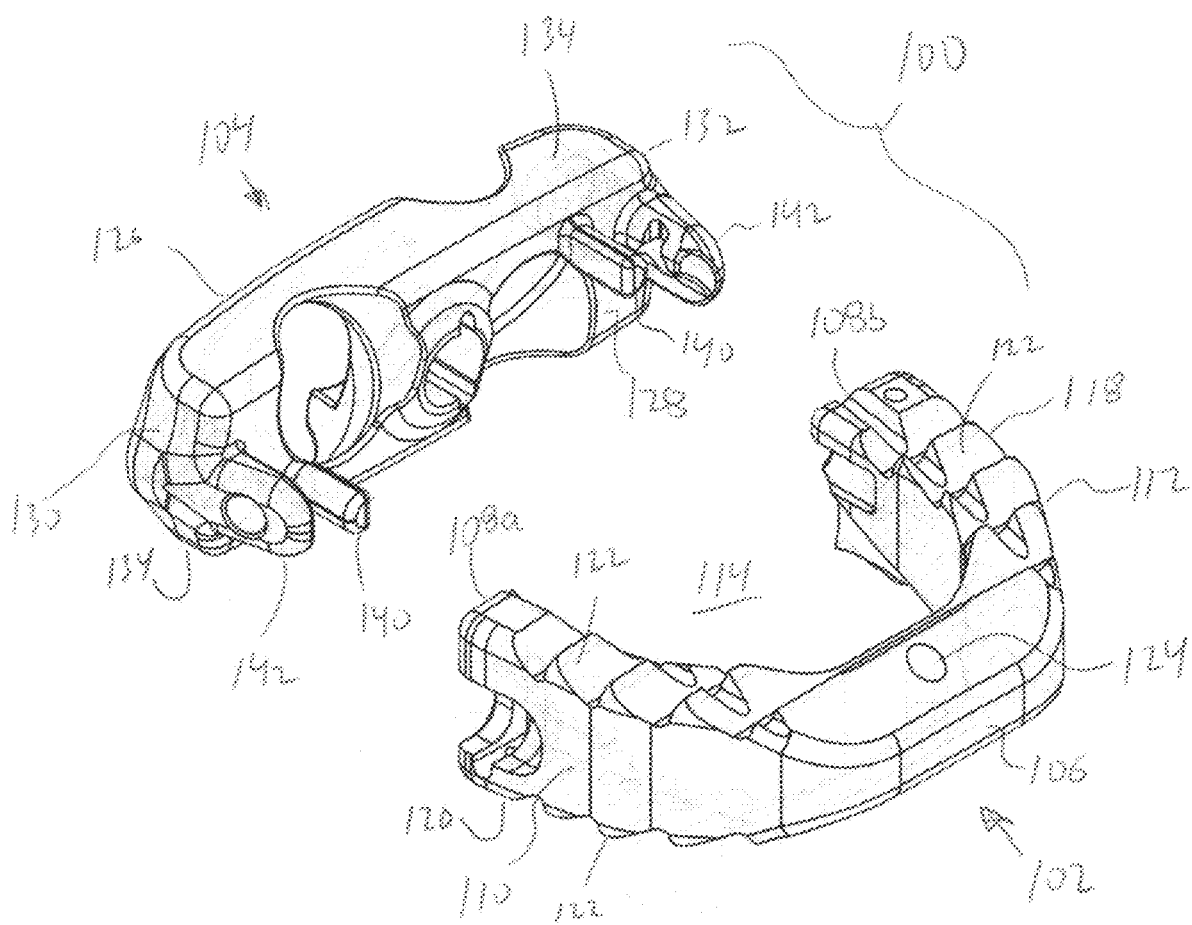
FIG. 3 shows an exploded perspective view showing one embodiment of a cervical interbody spacer

FIG. 3 is an exploded perspective view showing one embodiment of a cervical interbody spacer 100 comprising a spacer body 102 and a cervical plate 104 having coupling features to rigidly affixed the spacer body 102 to the cervical plate 104.

The spacer body 102 is u-shape having a closed distal end 106 and open proximal ends 108a, 108b connected by lateral sides 110, 112 with a central opening 114. The spacer body further includes an upper surface 118 and lower surface 120. The upper and lower surfaces 118, 120 may include teeth 122. The proximal end 108a, 108b of the spacer body 102 includes one or more bores or slots 144 and one or more slots 146 in the proximal portion of the right and left sides 130, 132. The spacer body 102 may also include a marker pin 124 for locating the spacer 100 on x-ray. The cervical plate is made of PEEK or titanium (TI).

The cervical plate 104 includes a proximal end 126, a distal end 128 and right and left sides 130, 132. The cervical plate further includes an upper surface 134 and lower surface 136. The upper and lower surfaces 134, 136 may include teeth 138. The distal end 128 includes one or more protrusions 140 configured to engage and to slide into the one or more bores or slots 144 and engagement arms 142 configured to engage and to slide into the one or more slots 146. The cervical plate is made of a rigid material, such as titanium (TI). The engagement arms 142 are design not to flex.

FIG. 4 is a proximal view of the spacer body 102 showing locking geometry, including the one or more bores or slots 144 and the one or more slots 146 in the proximal portion of the right and left sides 130, 132.

FIG. 5 is a sectional view at A-A of the spacer body 102 showing flexible locking pins 148 positioned in the slots 146. There are also pin distraction pockets 150 proximate the flexible locking pins 148 that are sized for the pin 148 to flex into during insertion of the engagement arms 142 of the cervical plate 104.

FIG. 6 is a top view of the cervical plate 104 showing the one or more protrusions 140 and engagement arms 142 configured to slide into the one or more bores or slots 144 and one or more slots 146 during joining of the spacer body 102 and cervical plate 104. The engagement arms 142 having features designed to engage with the flexible locking pins 148 to lock the spacer body 102 and cervical plate 104 together. The engagement arms 142 features may include distraction geometry 152 and lock geometry 154. The distraction geometry 152 includes an inclined or ramped portion 156 and the lock geometry 154 includes a pin engagement recess or pocket 158. The distraction geometry 152 is such that as the engagement arms 142 are slid into the slots 146, the inclined or ramped portions 156 engage flexible locking pins 148. Since the engagement arms 142 do not flex, the engagement forces the flexible locking pins 148 to deform or flex into the pin distraction pockets 150. Once the cervical plate 102 and spacer body 104 are completely joined, the flexible locking pins 148 reach the lock geometry recess or pockets 158, allowing the flexible locking pins 148 to return to their original form in the slot 146, thereby locking the spacer body 102 and cervical plate 104. The flexible locking pins 148 engaging the recess may provide an audible click sound the let the user know that the parts are joined and locked together.

Figure 7:
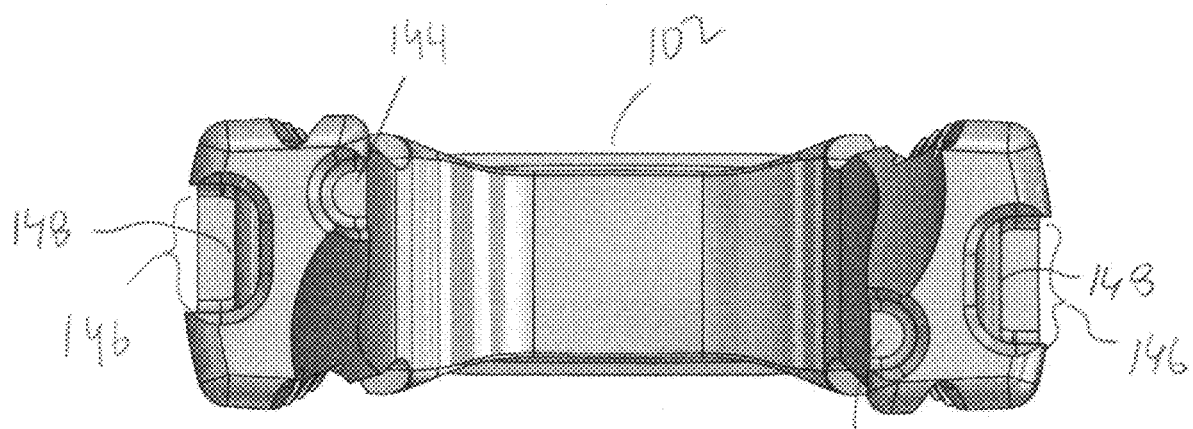
FIG. 7 shows a proximal view of the spacer body
Figure 8:
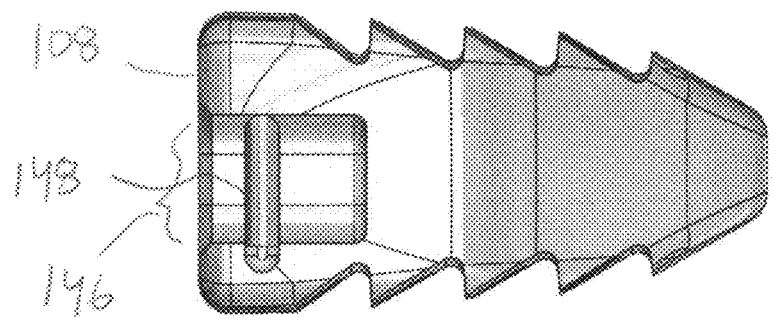
FIG. 8 shows a side view of the spacer body.

FIG. 7 is a proximal view and FIG. 8 is a side view of the spacer body 102 showing the one or more bores or slots 144 and slots 146 and flexible locking pins 148.

Figure 9:
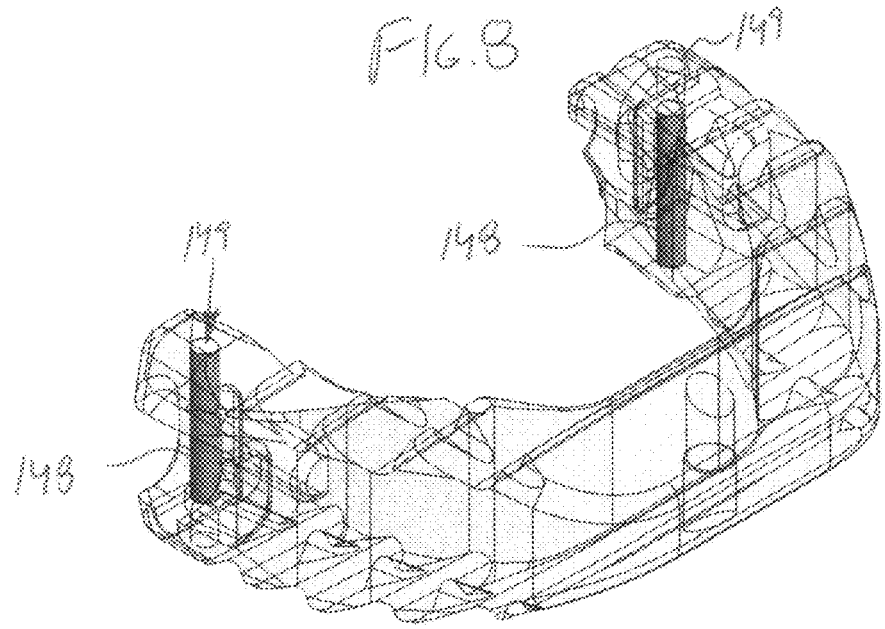
FIG. 9 shows a perspective view of spacer body that is shown as transparent.

FIG. 9 is a perspective view of spacer body 102 that is shown as transparent showing the locations of the locking pins 148. The flexible locking pins 148 are press-fit into holes 149 of the spacer body 102.

FIG. 10 is a perspective view and FIG. 11 is a top view of the cervical plate 140 and flexible locking pins 148 in the locked position. The flexible locking pins 148 are positioned within the recess or pocket 158 of the engagement arms 142.

In some embodiments, the spacer 100 will utilize a PEEK or titanium (TI) spacer body 102 in conjunction with a TI cervical plate 104 that can be assembled on the back table in the operating room. The cervical plate 104 will be rigidly affixed to the spacer body 102 via two flexible locking pins 148 press fit into the PEEK or TI spacer body and distraction/lock geometry present on the plate engagement arms 142.

While assembling the cervical plate 104 to the spacer body 102 the geometry of the cervical plate 104 is such that it will force the flexible locking pins 148 to deform into a relief pocket 150 present on the spacer body 102. Once the cervical plate 104 has been sufficiently inserted into the spacer body 102 the lock geometry on the cervical plate 104 will allow for the flexible locking pins 148 to return to its original form, thereby rigidly locking the cervical plate 104 to the spacer body 102.

The locking features of the present invention only requires relatively small amounts of assembly force due to the elasticity of the flexible locking pins, in addition, the flexible locking pins can be easily distracted utilizing a secondary instrument, allowing for simple and fast spacer disassembly.

2$^{nd}$ Embodiment—Flexible Locking Pins Positioned in the Cervical Plate

Figure 12:
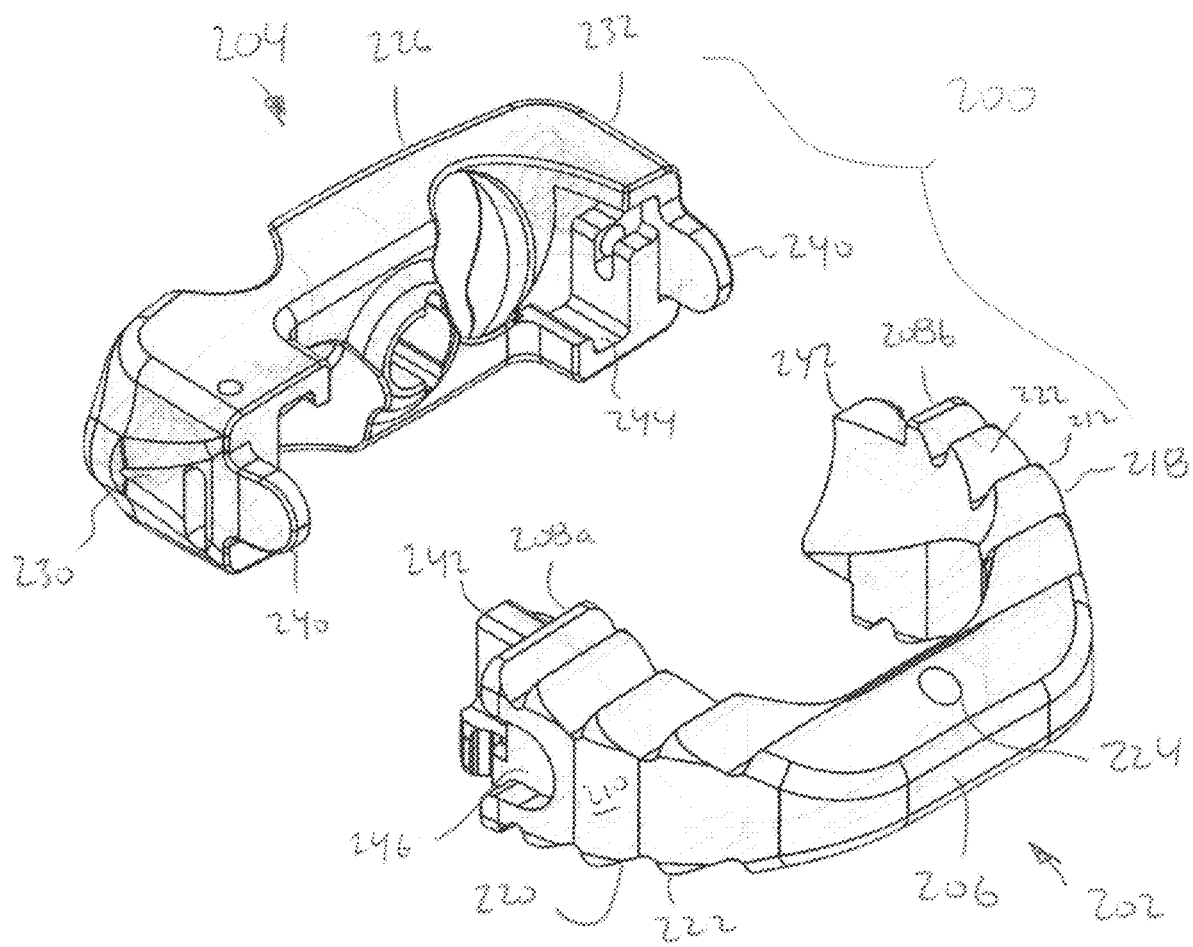
FIG. 12 shows an exploded perspective view showing another embodiment of a cervical interbody spacer

FIG. 12 is an exploded perspective view showing another embodiment cervical interbody spacer 200 comprising a spacer body 202 and a cervical plate 204 having coupling features to rigidly affixed the spacer body 202 to the cervical plate 204. The spacer body 202 and cervical plate 204 are similar to spacer 102 and cervical plate 104 discussed above, but the spacer body 202 includes attachment arms and the flexible locking pins are located in the cervical plate 204.

The spacer body 202 is u-shape having a closed distal end 206 and open proximal ends 208a, 208b connected by lateral sides 210, 212 with a central opening 214. The spacer body further includes an upper surface 218 and lower surface 220. The upper and lower surfaces 218, 220 may include teeth 222. The proximal end 208a, 208b of the spacer body 202 includes engagement arms 242 configured to engage and lock the spacer body 202 to the cervical plate 204 and side slots 246 (discussed below). The spacer body 202 may also include a marker or locating pin 224 for locating the spacer 200 on x-ray.

The cervical plate 204 includes a proximal end 226, a distal end 228 and right and left sides 230, 232. The cervical plate further includes an upper surface 234 and lower surface 236. The upper and lower surfaces 234, 236 may include teeth 238. The distal end 228 includes one or more alignment tabs 240 configured to couple with the slots 246.

Figure 13:
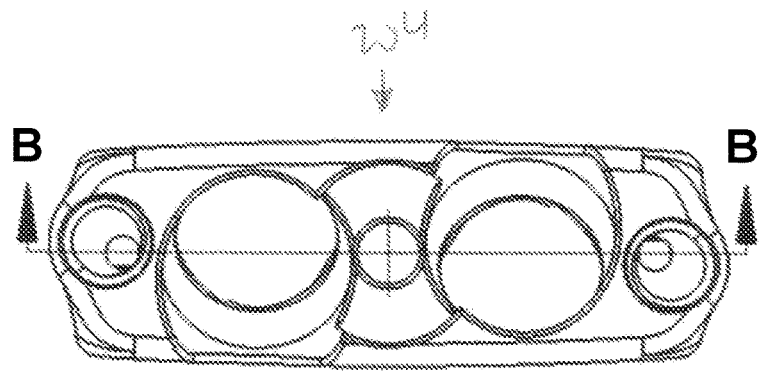
FIG. 13 shows a proximal view of the cervical plate.
Figure 14:
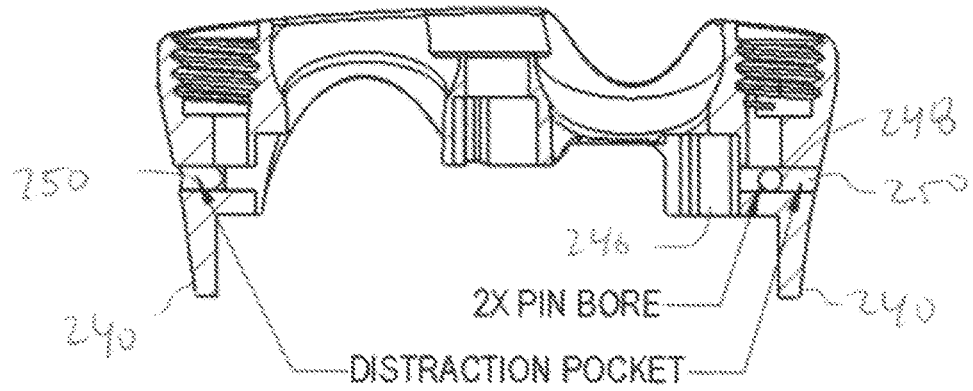
FIG. 14 shows a sectional view at B-B of the cervical plate shown in FIG. 13.

FIG. 13 is a proximal view and FIG. 14 is a sectional view at B-B of the cervical plate 204 showing the flexible locking pins 248 positioned in the slots 246. There are also pin distraction pockets 250 proximate the flexible locking pins 248 that are sized for the pin 248 to flex into during insertion of the engagement arms 242 of the spacer body 202.

Figure 15:
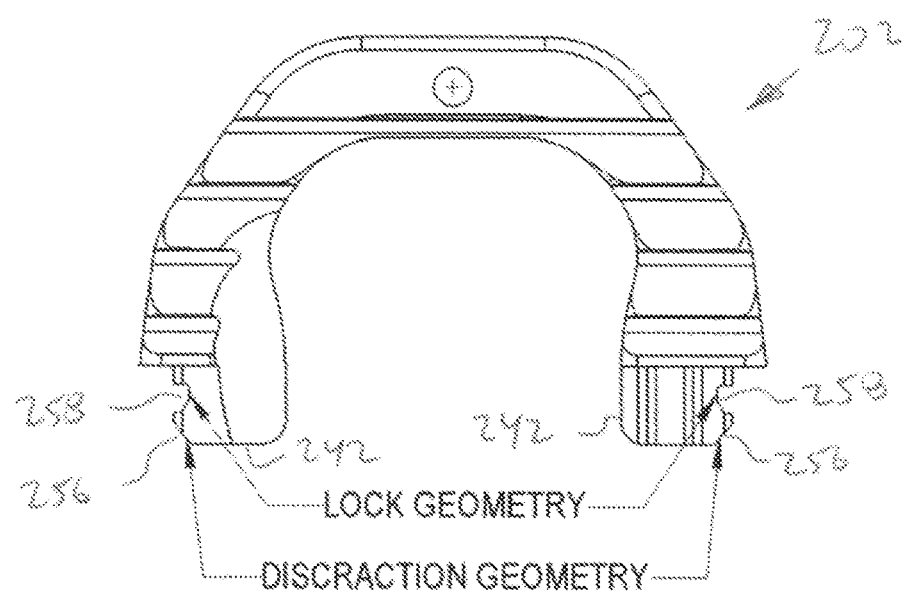
FIG. 15 shows a top view of the spacer body.

FIG. 15 is a top view of the spacer body 202 showing the engagement arms 242 having features designed to engage with the flexible locking pins 248 to lock the spacer body and cervical plate together. The engagement arms 242 features may include distraction geometry 252 and lock geometry 254. The distraction geometry includes an inclined or ramped portion 256 and the lock geometry includes a pin engagement recess or pocket 258. The distraction geometry 252 is such that as the engagement arms 242 are slid into the slots 246, the inclined or ramped portion 256 engages and forces the flexible pin 248 to deform or flex into the pin distraction pockets 258. Once the cervical plate and spacer body are completely joined, the flexible pin 248 reaches the lock geometry recess or pocket 258, allowing the flexible pin 248 to return to its original form in the slot 246, thereby locking the spacer body and cervical plate. The flexible locking pins 248 engaging the recess may provide an audible click sound the let the user know that the parts are joined and locked together.

Figure 16:
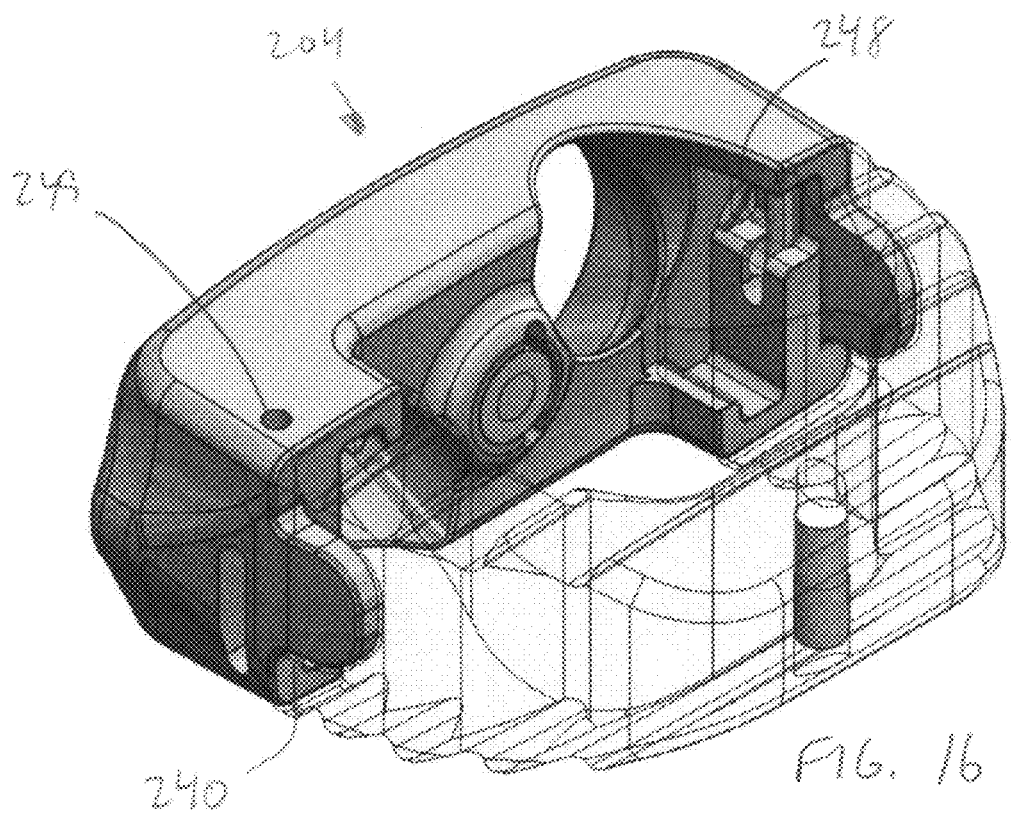
FIG. 16 shows a perspective view of cervical plate that is shown as transparent.

FIG. 16 is a perspective view of cervical plate 204 that is shown as transparent showing the locations of the flexible locking pins 248. The flexible locking pins 248 are inserted into holes 249 of the cervical plate 204.

Figure 17:
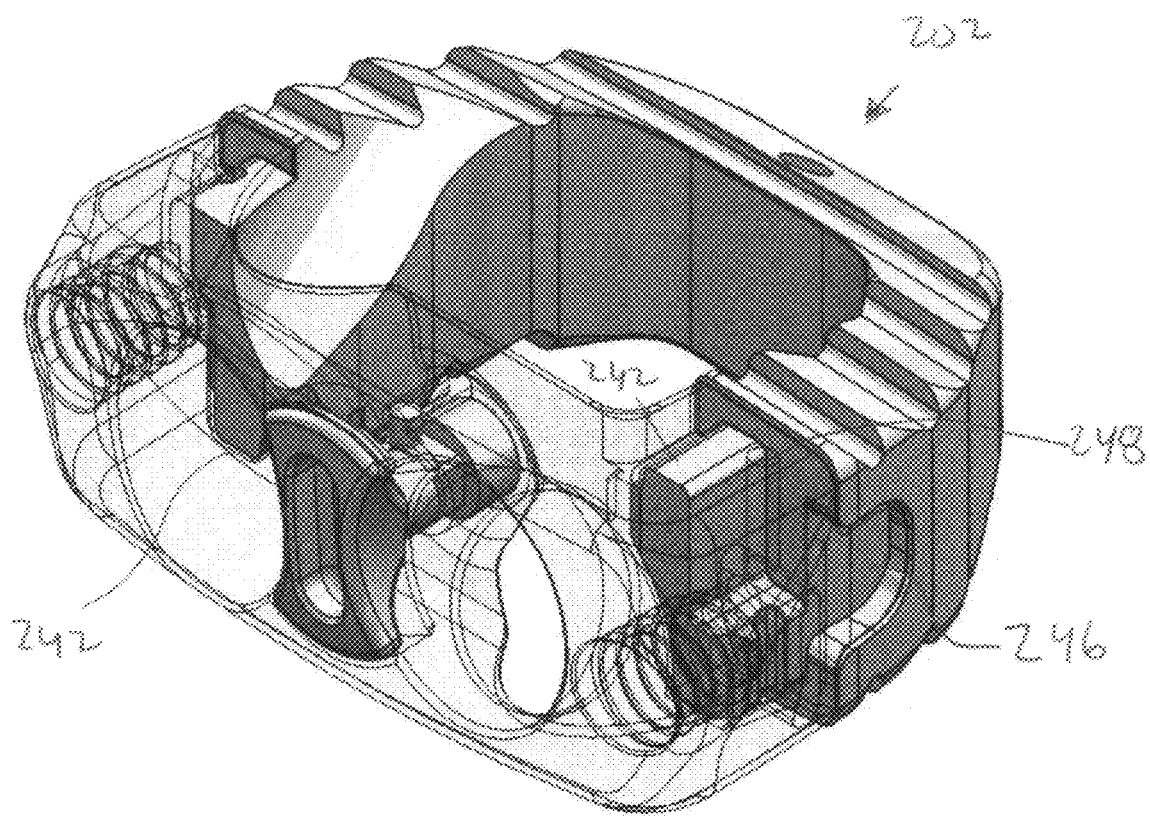
FIG. 17 shows a perspective view of the spacer body and cervical plate, shown as transparent.
Figure 18:
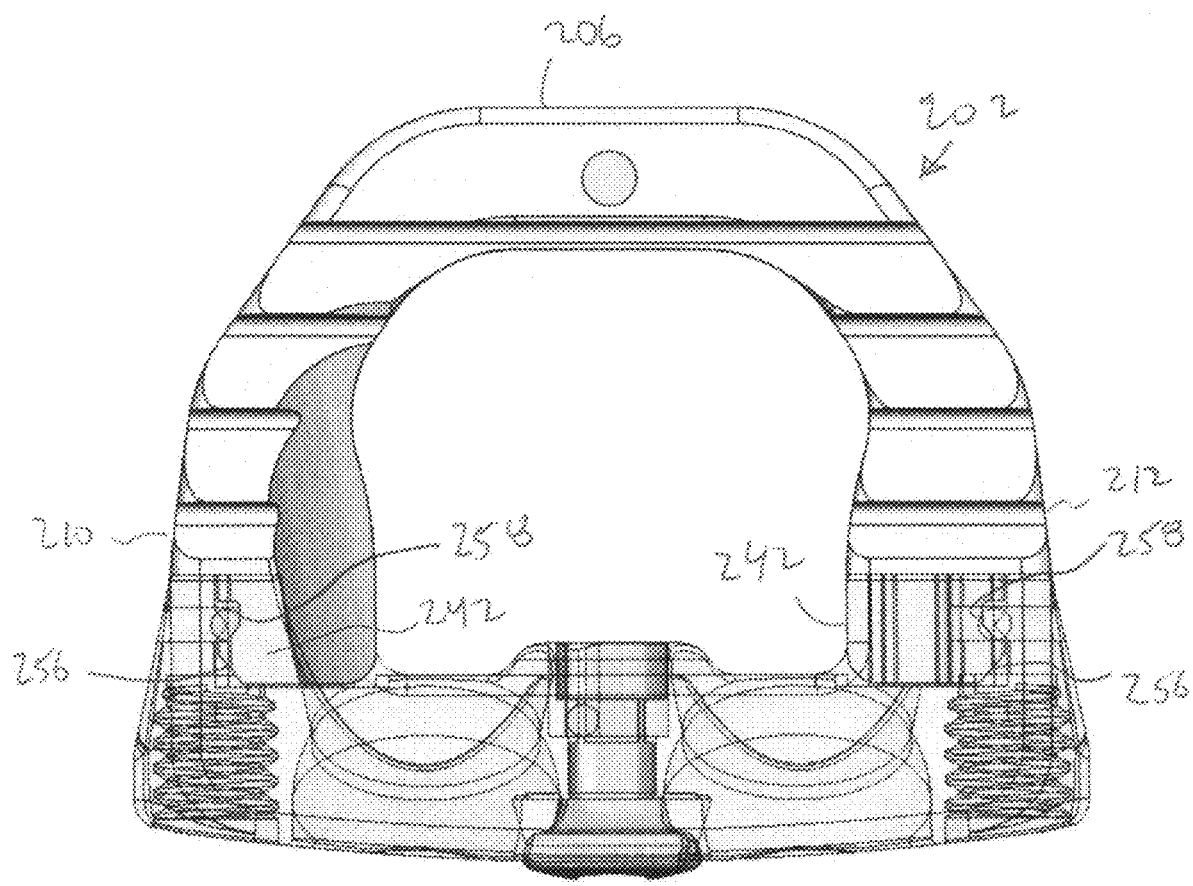
FIG. 18 shows a top view of the spacer body and cervical plate, shown as transparent.
Figure 19:
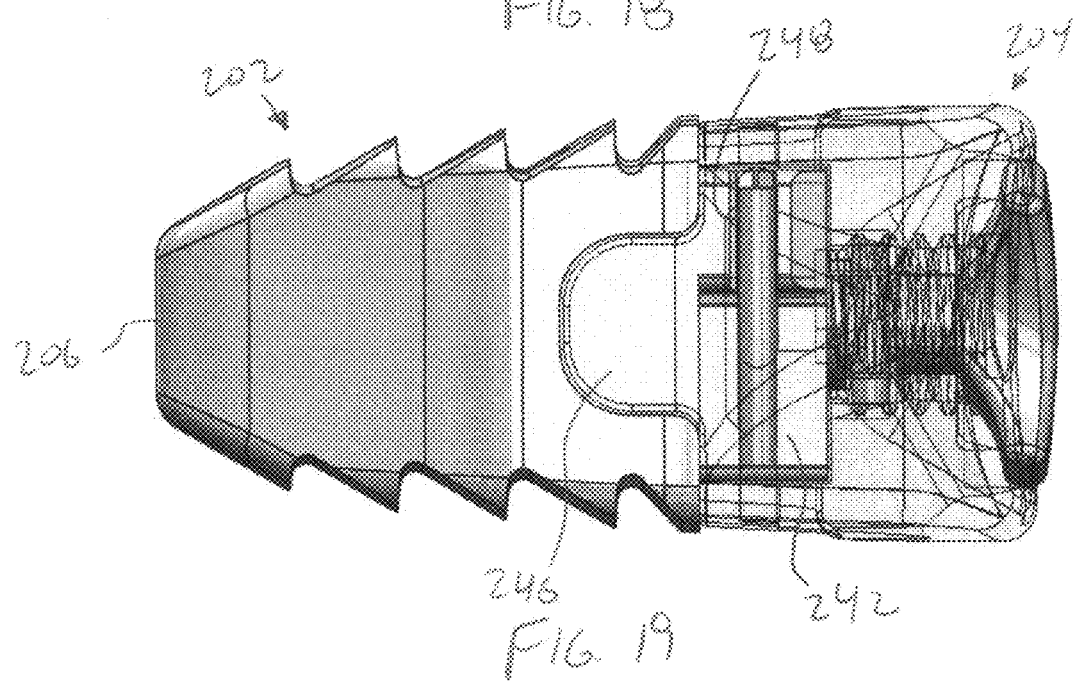
FIG. 19 shows a side view of the spacer body and cervical plate, shown as transparent.

FIG. 17 is a perspective view, FIG. 18 is a top view and FIG. 19 is a side view of the spacer body 202 and cervical plate 204, shown as transparent, showing the locking features. The flexible locking pins 248 are positioned within the recess or pocket 258 of the engagement arms 242.

In some embodiments, the spacer 200 will utilize PEEK or TI spacer body 202 in conjunction with a TI cervical plate 204 that will be assembled on the back table in the OR. The cervical plate 204 will be rigidly affixed to the spacer body 202 via two flexible locking pins 248 slip fit into holes 249 in the TI cervical plate 204 and swaged to retain. The spacer body 202 contains distraction/lock geometry for the flexible locking pins 248.

While assembling the cervical plate 204 to the spacer body 202 the geometry of the spacer body 202 is such that it will force the flexible locking pins 248 to deform into a relief pocket 250 present on the cervical plate 204. Once the cervical plate 204 has been sufficiently inserted into the spacer body 202 the lock geometry on the spacer body 202 will allow for the flexible locking pins 248 to return to its original form, thereby locking the cervical plate 204 to the spacer body 202.

As described above, the locking features of the spacer are designed to engage with one or more flexible locking pins to lock the spacer body and cervical plate together. The locking features are part of the engagement arm or engagement protrusion with a locking pin engagement surface having distraction geometry and lock geometry. The distraction geometry includes an inclined or ramped portion and the lock geometry includes a pin engagement recess or pocket. The distraction geometry of the locking pin engagement surface is such that as the spacer body and cervical plate are coupled, the inclined or ramped portion will engage and force the flexible pin to deform and slide on the surface. Once the cervical plate and spacer body are completely joined, the flexible pin reaches the lock geometry recess or pocket, allowing the flexible locking pins to return to its original form in the recess or pocket, thereby locking the spacer body and cervical plate. The flexible pin engaging the recess may provide an audible click sound the let the user know that the parts are joined and locked together.

Referring back to FIG. 1, the cervical plate 104, 204 includes two more fastener holes sized to receive bone engagement fasteners (not shown) configured to anchor the spacer 100 between two vertebrae of the spine. The cervical plates may also include a bone fastener locking feature to prevent the bone fastener from withdrawing from the fastener holes.

Cervical plate 104a includes two fastener holes, one fastener hole is tilted at an upward angle so that the engagement fastener engages the vertebra above the spacer and the other fastener hole is tilted at a downward angle so that the bone engagement fastener engages the vertebra below the spacer. Cervical plate 104b includes three fastener holes, a center fastener hole tilted at a downward angle so that the bone engagement fastener engages the vertebra below the spacer and two outer holes are tilted at an upward angle so that the engagement fasteners engage the vertebra above the spacer. Cervical plate 104c includes four fastener holes, an upper pair of fastener holes tilted at an upward angle so that the engagement fasteners engage the vertebra above the spacer and a lower pair of fastener holes tilted at a downward angle so that the bone engagement fasteners engage the vertebra below the spacer.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A cervical interbody spacer for placement between adjacent vertebrae comprising:
   a spacer body having lateral sides with side slots and pin distraction pockets in a proximal end;
   a cervical plate having attachment arms configured to slide into the side slots of the spacer body, the attachment arms having pin engagement recesses; and
   flexible locking pins positioned within the side slots proximate the distraction pockets;

wherein when the attachment arms are slid into the side slots, the flexible locking pins are configured to flex into the pin distraction pockets until the cervical plate and spacer body are completely joined and the flexible pins fixedly couple with the pin engagement recesses and lock the spacer body and plate.

2. The cervical interbody spacer of claim 1, wherein the attachment arms include inclined or ramped portions configured to engage and force the flexible pins to deform into the pin distraction pockets.

3. The cervical interbody spacer of claim 1, wherein the flexible pins are press-fit into holes of the spacer body.

4. The cervical interbody spacer of claim 1, wherein the flexible pins are made of nitinol.

5. The cervical interbody spacer of claim 1, wherein the proximal end of spacer body includes one or more bores and the cervical plate includes one or more protrusions configured to engage and to slide into the one or more bores.

6. The cervical interbody spacer of claim 1, wherein the spacer body is a u-shape having a closed distal end and open proximal end with a central opening.

7. The cervical interbody spacer of claim 1, wherein the spacer body is made of PEEK or titanium.

8. The cervical interbody spacer of claim 1, wherein the plate is made of titanium.

9. The cervical interbody spacer of claim 1, wherein the cervical plate includes two or more fastener holes sized to receive bone engagement fasteners.

10. A cervical interbody spacer for placement between adjacent vertebrae comprising:
   a cervical plate having lateral sides with side slots and pin distraction pockets in a distal end;
   a spacer body having engagement arms with pin engagement recesses configured to slide into the side slots of the cervical plate;
   flexible locking pins positioned within the side slots proximate the pin distraction pockets;
   wherein when the engagement arms are slid into the side slots, the flexible locking pins are configured to flex into the pin distraction pockets until the cervical plate and spacer body are completely joined and the flexible pins fixedly couple with the pin engagement recesses and lock the spacer body and plate.

11. The cervical interbody spacer of claim 10, wherein the engagement arms include inclined or ramped portions configured to engage and force the flexible pins to deform into the pin distraction pockets.

12. The cervical interbody spacer of claim 10, wherein the flexible pins are press-fit into holes of the cervical plate.

13. The cervical interbody spacer of claim 10, wherein the flexible pins are made of nitinol.

14. The cervical interbody spacer of claim 10, wherein the spacer body includes one or more side slots and the distal end of the cervical plate includes one or more alignment tabs configured to engage and to slide into the one or more side slots.

15. The cervical interbody spacer of claim 10, wherein the spacer body is a u-shape having a closed distal end and open proximal end with a central opening.

16. The cervical interbody spacer of claim 10, wherein the spacer body is made of PEEK or titanium.

17. The cervical interbody spacer of claim 10, wherein the plate is made of titanium.

18. The cervical interbody spacer of claim 10, wherein the cervical plate includes two or more fastener holes sized to receive bone engagement fasteners.

19. A cervical interbody spacer for placement between adjacent vertebrae comprising:
   a spacer body having lateral sides with side slots and pin distraction pockets in a proximal end;
   a cervical plate having attachment arms configured to slide into the side slots of the spacer body, the attachment arms having inclined or ramped portions and pin engagement recesses, the inclined or ramped portions configured to engage and force the flexible pins to deform into the pin distraction pockets; and
   flexible locking pins positioned within the side slots proximate the distraction pockets;
   wherein when the attachment arms are slid into the side slots, the flexible locking pins are configured to flex into the pin distraction pockets until the cervical plate and spacer body are completely joined and the flexible pins fixedly couple with the pin engagement recesses and lock the spacer body and plate.

20. The cervical interbody spacer of claim 19, wherein the proximal end of spacer body includes one or more bores and the cervical plate includes one or more protrusions configured to engage and to slide into the one or more bores.

* * * * *